(12) United States Patent
Golemis et al.

(10) Patent No.: US 6,326,150 B1
(45) Date of Patent: Dec. 4, 2001

(54) YEAST INTERACTION TRAP ASSAY

(75) Inventors: Erica Golemis, Oreland; Ilya Serebriiskii, Philadelphia, both of PA (US); Vladimir Khazak, Princeton, NJ (US)

(73) Assignee: Fox Chase Cancer Center, Philadelphia, PA (US)

( * ) Notice: Subject to any disclaimer, the term of this patent is extended or adjusted under 35 U.S.C. 154(b) by 0 days.

(21) Appl. No.: 09/508,803

(22) PCT Filed: Sep. 16, 1998

(86) PCT No.: PCT/US98/19353

§ 371 Date: Mar. 16, 2000

§ 102(e) Date: Mar. 16, 2000

(87) PCT Pub. No.: WO99/14319

PCT Pub. Date: Mar. 25, 1999

Related U.S. Application Data

(60) Provisional application No. 60/059,065, filed on Sep. 16, 1997.

(51) Int. Cl.$^7$ .............................. C12Q 1/68; C12N 15/81; C12N 1/19
(52) U.S. Cl. ........................... 435/6; 435/7.1; 435/320.1; 435/254.2; 435/254.21
(58) Field of Search ............................ 435/320.1, 6, 7.1, 435/254.2, 254.21

(56) References Cited

U.S. PATENT DOCUMENTS 6,074,829 * 6/2000 Hurd et al. ............................... 435/6

OTHER PUBLICATIONS

M.J. Grossel et al., "A yeast two–hybrid system for discerning differential interactions using multiple baits"; Nat. Biotech, vol. 17, Dec. 1999, pp. 1232–1233.

C. Inouye et al., "Mutational analysis of STE5 in the yeast *Saccaromyces cerevisiae*; application of differential interaction trap assay for examining protein–protein interactions"; Genetics (Oct. 1997), vol. 147, pp. 479–492.

R. Jiang et al., "Glucose regulates protein interactions within the yeast SNF1 protein kinase complex"; Genes Dev., 1996, vol. 10, pp. 3105–3115.

I. Serebriiskii et al., "A two–hybrid dual bait system to discriminate specificity of protein interactions"; J. Biol. Chem., Jun. 11, 1999, vol. 274, No. 24, pp. 17080–17087.

C. Xu et al., "Cells that register logical relationships among proteins"; Proc. Natl. Acad. Sci. USA, Nov. 1997, vol. 94, pp. 12473–12478.

S. Fields et al., "A novel genetic system to detect protein–protein interactions"; Nature, Jul. 20, 1989, vol. 340, pp. 245–246.

C. Chien et al., "The two–hybrid system; A method to identify and clone genes for proteins that interact with a protein of interest"; Proc. Natl. Acad. Sci. USA, Nov. 1991, vol. 88, pp. 9578–9582.

J. Gyuris et al., "Cdi1, a Human G1 and S Phase Protein Phosphate That Associates with Cdk2", Cell, Nov. 19, 1993, vol. 75, pp. 791–803.

J. Estojak et al., "Correlation of Two–Hybrid Affinity Data with In Vitro Measurements"; Molecular and Cellular Biology, Oct. 1995, vol. 15, No. 10, pp. 5820–5829.

* cited by examiner

*Primary Examiner*—David Guzo
(74) *Attorney, Agent, or Firm*—Dann, Dorfman, Herrell and Skillman

(57) ABSTRACT

The present invention provides an improved yeast interaction trap method and reagents for the detection of novel protein-protein interactions. The invention comprises a dual bait system which improves the accuracy of library screens with an immediate selection to eliminate false positives. The dual bait system of the present invention also allows for comparative, simultaneous assessment of interactions between two related members of a protein family or a wild-type versus mutated form of the same protein.

21 Claims, 8 Drawing Sheets

Figure 5C

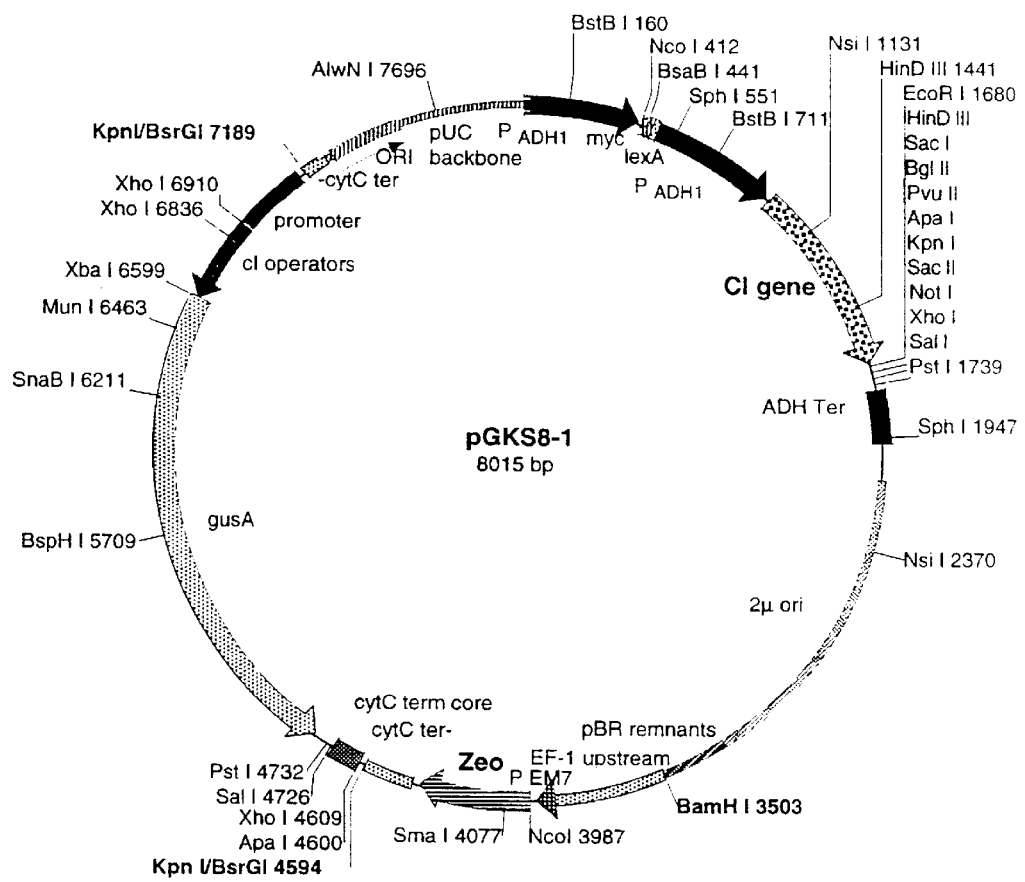

AAT frame

```
                                              SacII
         HinDIII      BglII       ApaI              NotI        SalI
  EcoRI         SacI        PvuII        KpnI            XhoI        PstI
G AAT TCA AGC TTG AGC TCA GAT CTC AGC TGG GCC CGG TAC CGC GGC CGC TCG AGT CGA Cct gca g
  N   S   S   L   S   S   D   L   S   W   A   R   Y   R   G   R   S   S   R   P   A
```

GAA frame

```
                                              SacII
         EcoRI        BglII       ApaI              NotI        SalI
            SacI            PvuII        KpnI            XhoI        PstI
AAT Ttg gaa ttC GAG CTC AGA TCT CAG CTG GGC CCG GTA CCG CGG CCG CTC GAG TCG ACc tgc ag
 N   L   E   F   E   L   R   S   Q   L   G   P   V   P   R   P   L   E   S   T   C
```

YEAST INTERACTION TRAP ASSAY

This application is a 371 of PCT/US98/19353 filed Sep. 16, 1998 which claims benefit of Prov. No. 60/059,065 filed Sep. 16, 1997.

FIELD OF THE INVENTION

This invention relates to the field of molecular biology. More specifically, the invention provides novel compositions and methods to facilitate the isolation and characterization of novel, protein-protein interactions involved in the regulation of cell growth and metabolism.

BACKGROUND OF THE INVENTION

Several publications are referenced in this application by numerals in parenthesis in order to more fully describe the state of the art to which this invention pertains. Full citations for these references are found at the end of the specification. The disclosure of each of these publications is incorporated by reference herein.

Biological regulatory systems require the specific organization of proteins into multi-component complexes. Two-hybrid systems have been used to identify novel components of signaling networks based on interactions with defined partner proteins (1–5). An important consideration in use of two-hybrid systems has been the degree to which interacting proteins distinguish their biological partner from evolutionarily conserved related proteins, and the degree to which observed interactions are specific.

In the basic version of the Yeast Interaction Trap Assay (20; FIG. 1A herein), the plasmid pEG202 or a related vector is used to express the probe or "bait" protein as a fusion to the heterologous DNA binding-protein LexA. Many proteins, including transcription factors, kinases and phosphatases, have been successfully used as bait proteins. The essential requirements for the bait protein are that it should not be actively excluded from the yeast nucleus, and it should not possess an intrinsic ability to strongly activate transcription. The plasmid expressing the LexA fusion bait protein is used to transform the yeast possessing a dual reporter system responsive to transcriptional activation through the Lex A operator. In one such example, the yeast strain EGY48 contains the reporter plasmid pSH18-34. In this case, binding sites for LexA are located upstream of two reporter genes. In the EGY48 strain, the upstream activating sequences of the chromosomal LEU2 gene, required for the biosynthesis of leucine, are replaced with LexA operator DNA binding sites. pSH18-34 contains a LexA operator-lacZ fusion gene. These two reporters allow selection for transcriptional activation by permitting selection for viability when cells are plated on medium lacking Leu, and discrimination based on color when the yeast is grown on medium containing X-gal.

In the basic protocol, EGY48/pSH18-34 transformed with a bait is characterized for its ability to express the fusion protein, growth on medium lacking leu, and for the level of transcriptional activation of lacZ.

In an interactor hunt, the strain EGY48/pSH18-34 containing the bait expression plasmid is transformed with a conditionally expressed library made in the vector pJG-5. This library uses the inducible yeast Gal1 promoter to express proteins as fusions to an acidic domain ("acid blob") that functions as a portable transcriptional activation motif. Expression of library-encoded proteins is induced by plating transformants on medium containing galactose (Gal), and the yeast cells are subsequently plated in gal medium lacking leucine. Yeast cells containing library proteins that do not interact specifically with the bait protein will fail to grow in the absence of Leu. Yeast cells containing library proteins that interact with the bait protein will form colonies within 2–5 days, and the colonies will turn blue when the cells are streaked on gal medium containing Xgal. The cells will not grow or turn blue on glucose medium—leucine+ Xgal. The plasmids are isolated and characterized by a series of tests to confirm specificity of the interaction with the initial bait protein. Those found to be specific are ready for further analysis. Thus, in summary, existing reagents assay the interaction of an activation-domain-fused protein A with a DNA-binding-domain fused protein B by their ability to activate transcription of two DNA-binding domain responsive reporters using a single bait moiety.

Kits or systems for practicing the methods described above are commercially available. Typically such a kit includes several components, i.e., a bait expression plasmid, and activation domain fusion plasmid, and a lexA operator-LacZ reporter plasmid. The lexA operator-LEU-2 gene is present in the host yeast strain. The first vector or plasmid contains a promoter and may include a transcription termination signal functionally associated with the first chimeric gene in order to direct the transcription of the first chimeric gene. The first chimeric gene includes a DNA sequence that encodes a DNA-binding domain and a unique restriction site(s) for inserting a DNA sequence encoding a first test protein or protein fragment in such a manner that the first test protein is expressed as part of a hybrid protein with the means for replicating itself in the host cell and in bacteria. Also included in the first vector is a first marker gene, the expression of which in the host cell permits selection of cells containing the first marker gene from cells that do not contain the first marker gene. The kit also includes a second vector which encodes a second chimeric gene. The second chimeric gene also includes a promoter and a transcription termination signal to direct transcription. The second chimeric gene also includes a DNA sequence that encodes a transcriptional activation domain and a unique restriction site(s) to insert a DNA sequence encoding the second test protein or protein fragment into the vector, in such a manner that the second test protein is capable of being expressed as part of a hybrid protein with the transcriptional activation domain. In one embodiment, the DNA-binding domain of the first hybrid protein and the transcriptional activation domain of the second hybrid protein are derived from transcriptional activators having separate DNA-binding and transcriptional activation domains. However, the DNA binding domain can be from any protein that binds DNA. The second vector also includes a means for replicating itself in the host cell and in bacteria. The second vector also includes a second marker gene, the expression of which, in the host cell permits selection of cells containing the second marker gene from cells that do not contain the second marker gene. The kit also includes a host yeast strain. The host yeast strain contains the detectable gene having a binding site for the DNA-binding domain of the first hybrid protein. The binding site is positioned so that the detectable gene expresses a detectable protein when the detectable gene is activated by the transcriptional activation domain encoded by the second vector. Activation of the detectable gene is possible when the transcriptional activation domain is in sufficient proximity to the detectable gene as when it associates with the protein encoded by the first vector. The host yeast strain, by itself, is incapable of expressing a protein having a function of the first marker gene, the second marker gene, the DNA-binding domain, or the transcriptional activation domain. In using the kit of the prior art, the interaction of the first test protein and the second test protein in the host cell causes a measurably greater expression of the detectable gene than when the DNA-binding domain and the transcriptional activation domain are present, in the absence of an interaction between the first test protein and the second test protein. The detectable gene may encode an enzyme or other product that can be readily measured. Such measurable activity may include the ability of the cell to grow only when the marker gene is transcribed, or the presence of detectable enzyme activity only when the marker gene is transcribed. U.S. Pat. Nos. 5,283,173 and 5,580,736 disclose two variations of the original interaction trap assay. The disclosures of these two patents are incorporated by reference herein.

Certain difficulties have been experienced in implementing the systems described above. One particularly troublesome operational problem is the generation of non-specific false positives. Furthermore, it is clear that many biologically important proteins are organized into families of evolutionarily related members which conserve substantial sequence similarity (17–19). Thus, a question arises as to the degree to which two-hybrid systems isolate proteins specific for individual baits, rather than those which interact generally with a class of protein ("familial positives"). While existing two-hybrid systems allow discrimination of uniquely specific interactors from false positives or familial positives through use of various methods of specificity testing performed subsequent to a screen (20), these methods are frequently laborious, particularly when many possible interactors must be tested. For this reason, the present inventors have appreciated a need for reagents and methods to eliminate such clones prior to selection.

SUMMARY OF THE INVENTION

The present invention provides an adaptation of the two-hybrid system described above, which should essentially eliminate the inherent false-positive problems of the existing system. The dual bait yeast interaction trap assay of the present invention also allows for the simultaneous assay of protein interactions in a single step as well as the simultaneous assay of a protein interaction with two related or unrelated partners in a single cell. This latter property, in turn, enables a number of new potential uses for the two hybrid system, described in detail below.

Novel reagents that greatly enhance the reliability and general utility of two-hybrid systems are disclosed. Existing reagents assay the interaction of an activation-domain-fused Protein A with a DNA-binding-domain-fused Protein B by their ability to activate transcription of two DNA-binding-domain responsive reporters. In accordance with the present invention, the improved reagents comprise a single strain of yeast which contains a dual-bait reporter system. Thus, an activation-domain-fused Protein A with a unique specific partner will interact with DNA-binding-domain-1-fused Protein B to activate transcription of two DNA-binding-domain-1-responsive reporters, but will not interact with a DNA-binding-domain-2-fused Protein C to activate transcription of DNA-binding-domain-B responsive reporters. Compare FIGS. 1A and 1B. In this system, non-specific or false positives will activate all three reporter systems.

The improved reagents of the present invention will produce several major experimental benefits. First, they will allow library screens to be improved with an immediate selection to eliminate false positives. This will be especially critical in some applications, such as screening for RNA-motif-binding proteins, which have notably high backgrounds. Second, these reagents will allow comparative simultaneous assessment of interaction between an activation-domain-fused protein and two partner proteins, which might be two related members of a protein family, or a wild type versus a mutated form of the same protein. This alternative application is likely to be of particular use in conjunction with targeted drug discovery efforts. Third, the reagents of the present invention make it possible to perform two completely independent simultaneous screens with a single library transformation. Fourth, the reagents of the present invention utilize antibiotic resistance in addition to amino acid auxotrophy for the selection process. This approach provides greater latitude in the design of the reagents of the invention and enables the use of multiple reporters which respond to different baits. Additionally, the reagents of the present invention while designed for use in the Interaction Trap form of two-hybrid system, are readily adaptable to other currently existing two-hybrid systems (e.g., Fields' or Elledge's GAL4 based systems, or SOS membrane-associated two hybrid systems, or Hollenberg's LexA-based system).

In accordance with the claimed invention a method is provided for determining the interactions between a first and second protein of interest via the selective activation of dual bait based reporter systems. The method, referred to herein as the Dual Bait System, comprises providing a host cell with 1) a first reporter gene operably linked to a first protein binding site; 2) a second reporter gene operably linked to the protein binding site provided in 1); 3) a third reporter gene operably linked to a second protein binding site; 4) a first bait protein encoded by a first fusion gene, the first bait protein comprising the first protein of interest operably linked to a first binding moiety which effects specific binding of the first bait protein to the first protein binding site; 5) a second fusion-gene which encodes a second fusion protein, the second fusion protein comprising the second protein of interest operably linked to a gene activating moiety; 6) a second bait protein encoded by a third fusion gene, the second bait protein being different from the first bait protein and operably linked to a second binding moiety which effects specific binding of the second bait protein to the second protein binding site; and measuring interaction of the first and second proteins of interest via selective activation of the first, second and third reporter genes.

In a preferred embodiment of the invention, the method comprises the use of a fourth reporter gene operably linked to the second protein binding site as described in 3) above. See FIG. 1C. This embodiment is particularly suitable for the performance of two completely independent, simultaneous screens with a single library transformation. This embodiment facilitates the performance of counter-screens based on activation of the different reporters.

In yet another embodiment of the invention, the reagents described herein are used for incorporation into yeast with preselected genetic backgrounds. This system will facilitate the analysis of interacting proteins in yeast mutants thereby further elucidating the biochemical interactions that occur in such mutants.

The method of the present invention, as described above, may be practiced using an add-on kit which contains reagents to augment yeast interaction trap kits already available. Preferably, the kit of the present invention includes a container, and at least one vector for introduction into the host cells currently on the market. The additional vector includes a third reporter gene operably linked to a protein binding site distinct from the binding sites present in the proteins encoded by the first and second chimeric genes in the kit of the prior art. A second bait protein (hence the designation "dual bait") is also provided which is encoded by a third fusion gene, the second bait protein being distinct from the first bait protein encoded by the vectors present in the prior art kits. The second bait protein is operably linked to a second binding moiety which effects specific binding if the second bait protein to the second protein binding site. In a particularly preferred embodiment, a fourth vector construct is provided which includes a fourth reporter gene. Preferred plasmids for use in the methods of the present invention include pGKS8 which encodes a cI fusion and a cI operator-GUS reporter plus a selectable marker and replication sequences. This plasmid includes the second bait and the cIop-GUS reporter on the same plasmid, eliminating the need in this instance of a fourth vector construct. For using this plasmid, it is extremely desirable to utitilize the SKY48 yeast strain wherein the fourth reporter is present as an integrated auxotrophy. Accordingly, the kit of this invention may include strain SKY48. Plasmid pCIL-2 may also be used to advantage in the present invention. This plasmid facilitates simple one-step integration of cIoperator-LYS2 reporter into yeast of of any genetic background.

As used herein, "reporter gene" refers to a gene whose expression may be assayed; such genes include, without limitation, LacZ, β-glucuronidase (GUS), amino acid biosynthetic genes, e.g., the yeast LEU2, HIS3, LYS2, or URA3 genes, nucleic acid biosynthetic genes, the mammalian chloramphenicol transacetylase (CAT) gene, the green fluorescent protein (GFP) or any surface antigen gene for which specific antibodies are available.

A "promoter" is a DNA sequence located proximal to the start of transcription at the 5' end of an operably linked transcribed sequence. The promoter may contain one or more regulatory elements or modules which interact in modulating transcription of the operably linked gene.

"Operably linked" describes two macromolecular elements arranged such that modulating the activity of the first element induces an effect on the second element. In this manner, modulation of the activity of a promoter element may be used to alter and/or regulate the expression of an operably-linked coding sequence. For example, the transcription of a coding sequence that is operably-linked to a promoter element is induced by factors that "activate" the promoter's activity; transcription of a coding sequence that is operably-linked to a promoter element is inhibited by factors that "repress" the promoter's activity. Thus, a promoter region is operably-linked to the coding sequence of a protein if transcription of such coding sequence activity is influenced by the activity of the promoter.

"Fusion construct" refers generally to recombinant genes which encode fusion proteins.

A "fusion protein" is a hybrid protein, i.e., a protein which has been constructed to contain domains from at least two different proteins. As used herein, a fusion protein is a hybrid protein which possesses (a) transcriptional regulatory domain from a transcriptional regulatory protein, or (b) a DNA binding domain from a DNA binding protein linked to a heterologous protein to be assayed for interaction. The structure of the fusion protein is such that the transcriptional regulatory domain and the DNA binding domain are arranged in a manner that allows both domains to be biologically active. The protein that is the source of the transcriptional regulatory domain is different from the protein that is the source of the DNA binding domain. In other words, the two domains are heterologous to each other.

The transcriptional regulatory domain of the fusion protein may either activate or repress transcription of target genes, depending on the native biological activity of the domain.

The bait proteins of the invention are also fusion proteins encoded by a fusion gene which comprises a protein of interest operably linked to a DNA binding moiety.

The term "fusion protein gene" refers to a DNA sequence which encodes a fusion protein. A fusion protein gene may further provide transcriptional and translational regulatory elements for the transcriptional and translational control thereof.

"Expression" is the process by which the information encoded within a gene is revealed. If the gene encodes a protein, expression involves both transcription of the DNA into mRNA, the processing of mRNA (if necessary) into a mature mRNA product, and translation of the mature mRNA into protein.

A nucleic acid molecule, such as a DNA or gene is said to be "capable of expressing" a polypeptide if the molecule contains the coding sequences for the polypeptide and the expression control sequences which, in the appropriate host environment, provide the ability to transcribe, process and translate the genetic information contained in the DNA into a protein product, and if such expression control sequences are operably-linked to the nucleotide sequence that encodes the polypeptide.

As used herein, a "cloning vehicle" is any entity that is capable of delivering a nucleic acid sequence into a host cell for cloning purposes. Examples of cloning vehicles include plasmids or phage genomes. A plasmid that can replicate autonomously in the host cell is especially desired. Alternatively, a nucleic acid molecule that can insert (integrate) into the host cell's chromosomal DNA is useful, especially a molecule which inserts into the host cell's chromosomal DNA in a stable manner, that is, a manner which allows such molecule to be inherited by daughter cells.

Cloning vehicles are often characterized by one or a small number of endonuclease recognition sites at which such DNA sequences may be cut in a determinable fashion without loss of an essential biological function of the vehicle, and into which DNA may be spliced in order to bring about its replication and cloning.

The cloning vehicle may further contain a marker suitable for use in the identification of cells transformed with the cloning vehicle. For example, "a marker gene" may be a gene which confers resistance to a specific antibiotic on a host cell. The word "vector" is sometimes used interchangeably with "cloning vehicle".

As used herein, an "expression vehicle" is a vehicle or vector similar to the cloning vehicle but is especially designed to provide an environment which allows the expression of the cloned gene after transformation into the host. One manner of providing such an environment is to include transcriptional and translational regulatory sequences on such expression vehicle, such transcriptional and translational regulatory sequences being capable of being operably linked to the cloned gene. Another manner of providing such an environment is to provide a cloning site or sites on such vehicle, wherein a desired cloned gene and desired expression regulatory elements may be cloned.

In an expression vehicle, the gene to be cloned is usually operably-linked to certain control sequences such as promoter sequences. Expression control sequences will vary depending on whether the vector is designed to express the operably-linked gene in a prokaryotic or eukaryotic host and may additionally contain transcriptional elements such as enhancer elements, termination sequences, tissue-specificity elements, and/or translational initiation and termination sites.

A "host" refers to any organism that is the recipient of a cloning or expression vehicle. In preferred embodiments, the host of the invention is a yeast cell or a cultured animal cell such as a mammalian or insect cell. In an especially preferred embodiment, the yeast host is *Saccharomyces cerevisiae*.

A "binding moiety" is a stretch of amino acids which is capable of directing specific polypeptide binding to a particular DNA sequence (i.e., a "protein binding site"). Also referred to herein as a DNA binding domain, these proteins may be homodimers or monomers that bind DNA in a sequence specific manner. Exemplary DNA binding domains of the invention include LexA, cI, glucocorticoid receptor binding domains and the Ume6 domain.

A "gene activating moiety" is a stretch of amino acids which is capable of weakly inducing the expression of a gene to whose control region it is bound. As used herein, "weakly" is meant below the level of activation effected by GAL4 activation region II (Ma and Ptashne, Cell, 48: 347, 1987) and is preferably at or below the level of activation effected by the B42 activation domain of Ma and Ptashne (Cell, 51: 413, 1987). Levels of activation may be measured using any downstream reporter gene system and comparing, in parallel assays, the level of expression stimulated by the GAL4 region II-polypeptide with the level of expression stimulated by the polypeptide to be tested.

"Purified DNA" is DNA that is not immediately contiguous with both of the coding sequences with which it is immediately contiguous (one of the 5' end and one of the 3' end) in the naturally occurring genome of the organism from which it is derived. The term therefore includes, for example, a recombinant DNA which is incorporated into a vector; into an autonomously replicating plasmid or virus; or into the genomic DNA of a prokaryote or eukaryote, or which exists as a separate molecule (e.g., a cDNA or a genomic DNA fragment produced by PCR or restriction endonuclease treatment) independent of other sequences. It also includes a recombinant DNA which is part of a hybrid gene encoding additional polypeptide sequence.

"Substantially identical", in reference to an amino acid sequence, means an amino acid sequence which differs only by conservative amino acid substitutions, for example, substitution of one amino acid for another of the same class (e.g., valine for glycine, arginine for lysine, etc.) or by one or more non-conservative substitutions, deletions, or insertions located at positions of the amino acid sequence which do not destroy the function of the protein (assayed, e.g., as described herein). A "substantially identical" nucleic acid sequence codes for a substantially identical amino acid sequence as defined above.

A "transformed cell" is a yeast or bacterial cell into which (or into an ancestor of which) exogenous DNA has been introduced by means of recombinant DNA techniques.

The phrase "positioned for expression" refers to a DNA coding molecule which is positioned adjacent to a DNA sequence which directs transcription and translation of the sequence.

A "purified antibody" is an antibody at least 60 weight percent of which is free from the proteins and naturally-occurring organic molecules with which it is naturally associated. Preferably, the preparation comprises antibody in an amount of at least 75 weight percent, more preferably at least 90 weight percent, and most preferably at least 99 weight percent.

A "malignant cell" is a higher eucaryotic cell which has been released from normal cell division control. Included in this definition are transformed and immortalized cells.

BRIEF DESCRIPTION OF THE DRAWINGS

FIG. 1A shows the original Interaction Trap (4) of the prior system. FIG. 1B shows the Dual Bait system in which an activation domain-fused prey interacts with a LexA-fused bait to drive transcription of lexAop-responsive LEU2 and LacZ reporters, but does not interact with a cI-fused bait and thus does not turn on transcription of cIop-responsive LYS2 reporter.

FIGS. 5A, 5B and 5C depict vectors for use in the present invention. The original pEG202-based vector, pGKS3, with the His marker is shown in FIG. 5A and a pGKS6 vector is shown in FIG. 5B. In pGKS6, the His marker has been replaced with a Zeocin resistance marker. FIG. 5C depicts the pGKS8-1 vector which contains a fusion protein to cI, a zeocin selectable marker and a GUS reporter under control of cI operators (SEQ ID NOS: 2–5).

DETAILED DESCRIPTION OF THE INVENTION

Figure 1A:
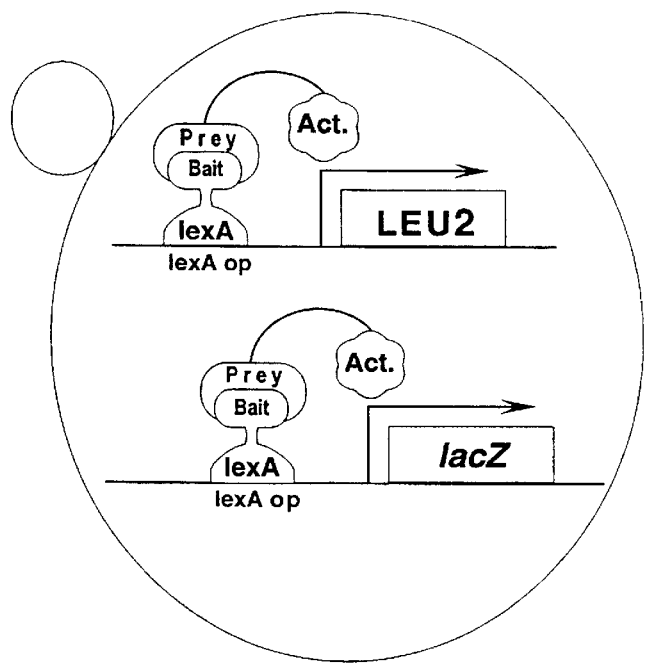
FIGS. 1A and 1B are schematic drawings comparing the original interaction trap system to the Dual Bait System of the present invention.

To understand and manipulate the function of a particular protein of biological interest, it is generally useful to identify other proteins with which it associates. While identification of protein interactions initially proceeded almost solely by technically difficult biochemical methods, in recent years yeast two-hybrid systems (1) have developed as a powerful genetic tool to rapidly select previously uncharacterized proteins that specifically interact with a target protein of interest from a suitable library (2–5). In this schema, a protein of interest is synthesized in yeast as a fusion to a DNA-binding-domain (DBD), which is typically the bacterial repressor protein LexA or the amino-terminal end of the yeast transcription factor GAL4. Interaction of this DBD-protein fusion (a "bait") with a transcriptional activation domain-fused partner protein (either a defined partner, or a novel protein screened from a library) allows the activation of reporter genes (LacZ, HIS3, LEU2) responsive to the cognate DBD. More recently, interest has focused on expanding the utility of two-hybrid systems, to enable the detection of interactions between proteins and RNA (6, 7), proteins and non-protein ligands (8), proteins and peptides (9, 10), and proteins and multiple partners (11, 12). A second thrust has been to enable whole-genome applications (13–15), leading to the generation of maps of protein interaction networks with the potential to complement the vast resource of sequence information now being developed as part of the Genome project. Finally, there has been interest in developing two-hybrid systems as tools in high throughput drug discovery screening strategies to identify agents regulating the activity of biologically important target proteins.

As two-hybrid technologies have evolved to more complex applications, a question of mounting importance has been the degree to which library screens performed in these systems yield partners specific for the utilized bait, as opposed to proteins of broad interaction capability (i.e., "false positives"). While the large number of published two-hybrid papers indicates that many specific partners are obtained, a recent survey has suggested that the majority of library screens isolate at least some cDNAs which are non-specific (16). As another consideration, it is clear that many biologically important proteins are organized into families of evolutionarily related members which conserve substantial sequence similarity (eg, 17–19). Thus, a related question has been the degree to which two-hybrid systems isolate proteins specific for individual baits, rather than those which interact generally with a protein class ("familial positives").

The "dual bait system" of the present invention may be sold in a kit which incorporates controls for false positives or non-specific interactions in a single step, and allows the simultaneous assay of a protein interaction with two related or unrelated partners in a single cell, which should be useful for a variety of high-throughput pharmacologically oriented studies. While these original reagents are built upon the interaction trap form of two-hybrid system (4), they have been constructed to potentially supplement any of the currently existing two-hybrid variants.

Materials & Methods for Example I
Molecular Biology and Genetic Techniques.

DH5α E. coli was grown on LB medium (21); where appropriate, antibiotics were added to concentrations recommended by suppliers. Standard DNA manipulation techniques were used (21). Yeast were grown on YPD or minimal medium, and manipulated using standard techniques (22). Two-hybrid experiments and β-galactosidase assays were performed as described (23), with six independent colonies assayed for each value presented; for a sensitive plate-based XGal assay, the procedure of (24) was used.

Dual Bait System Reagents

Relevant properties of all strains and plasmids are described in the text. The bacteriophage lambda repressor protein cI (25) was used as the basis of reagent development, as its size, structure, and DNA binding properties suggested it might behave comparably as a DNA binding domain (DBD) to the pre-existing two-hybrid system DBD LexA (26–28).

cI-responsive LacZ Reporters

A 68 bp fragment of the lambda bacteriophage genome containing cI operators (LAMCG, nt 37950-38018) was amplified and XhoI ends added by PCR. The resulting product was digested with XhoI and inserted into the XhoI site of the plasmid LR1Δ1 (parent of all currently utilized interaction trap lexAop-LacZ reporters, (20)) in either orientation upstream of a basal GAL1 promoter directing expression of the LacZ gene. The resulting plasmids pcIop-LacZA and pcIop-LacZB have a 2μ origin of replication and use a URA3 marker for selection in yeast; they differ only in the orientation of the cI operator cassette.

cI-fusion Bait Vectors and Test Constructs

Figure 5A:
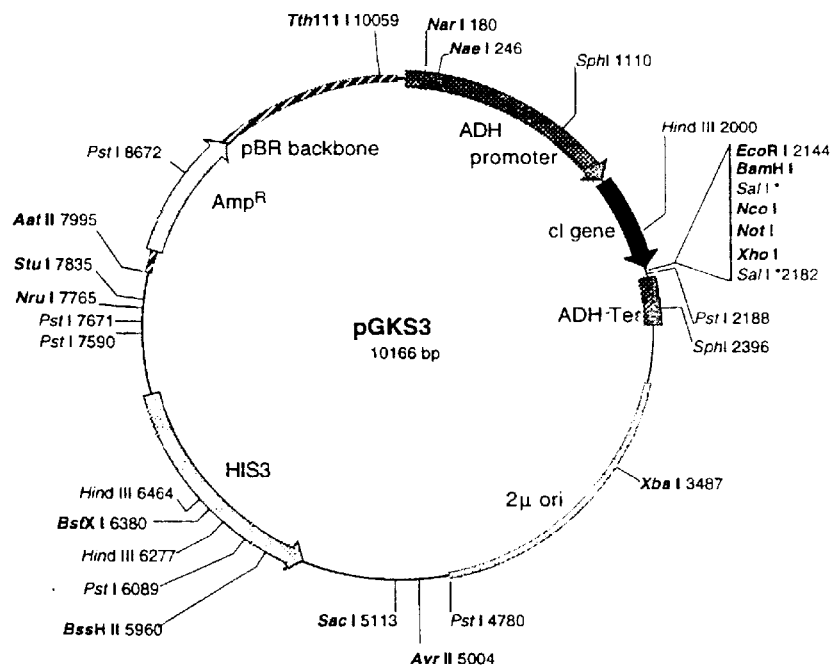
Figure 5B:
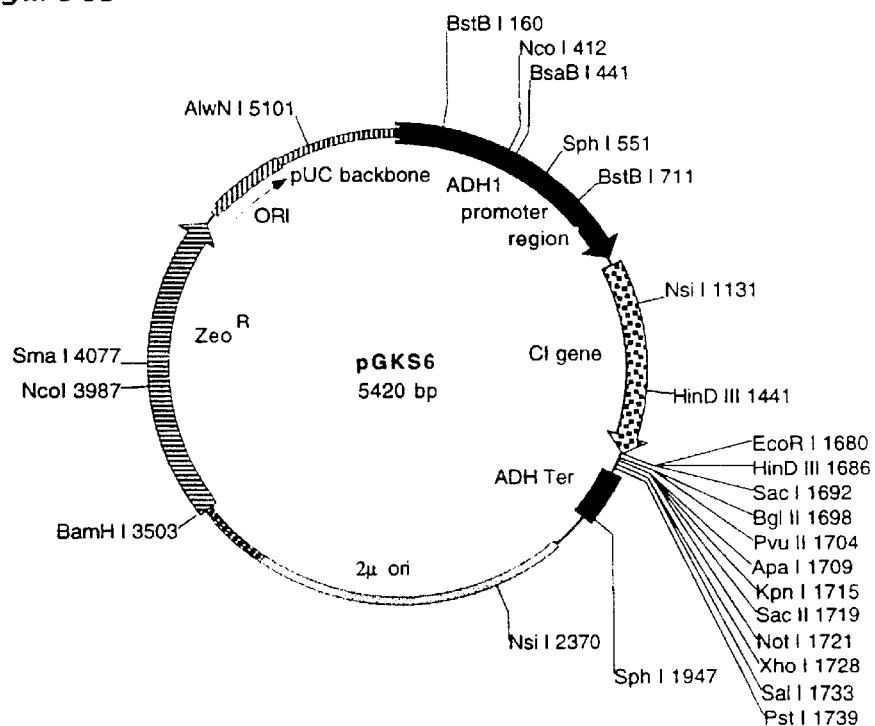

A DNA fragment containing the complete coding sequence (with no stop codon) for bacteriophage lambda cI repressor protein (LAMCG, nt 37230...37940) was amplified by PCR and cloned into pUC19 plasmid to yield pUC-cI. Separately, a HIS3-containing fragment of pEG202 was removed by AatII-ClaI digestion and replaced by a synthetic AatII-ClaI linker, to create pGK202. Subsequent HindIII digestion, fill-in reaction and EcoRI digestion were used to remove the LexA gene from pGK202, followed by replacement with the cI gene on a BglII(filled-in)-EcoRI fragment excised from pUC-cI. The resulting plasmid pGK302, was digested with BamHI and AatII and ligated to a BamHI-AatII fragment of pEG202 to create pGKS3, a pEG202 "sibling" with the cI gene exactly replacing the LexA gene. pGKS3 has a 2μ origin of replication, carries a HIS3 marker for selection in yeast, and was used in control experiments. Subsequently, a BsaBI-EcoRI fragment of pGKS3 (encompassing cI) was used to replace the LexA gene in the plasmid pLexZeo (Invitrogen) which had been digested with HpaI-EcoRI. The resulting plasmid, pGKS6, uses the ADH1 promoter to express a cI fusion. It has a 2μ origin of replication and uses Zeocin (Invitrogen) resistance for selection in yeast and bacteria. A DNA fragment containing a minimal Gal1 promoter, cI operator cassette and the translational start of the GAL1 gene (essentially the same as in cI responsive lacZ reporter) was used to direct the expression of the gusA gene. A gusA reporter cassette was inserted into the BsrGI site of pGKS6 in both orientations. One of the resulting plasmids with the lower gusA background was termed pGKS8 and utilized in further experiments. See FIG. 5. Expression of proteins was assayed by standard lysis of cells expressing appropriate constructs (20), followed by SDS-PAGE, and Western analysis with antibodies to Krev-1 (Transduction Labs, Inc.), LexA, or cI repressor (gift of G. Kalmar).

Baits and Prey

To create activating DBD-fused bait plasmids, the full-length Krit1 gene (29) was inserted into EcoRI-XhoI digested pGKS3, pGKS6 or pEG202. Non-activating bait fusions were constructed by cloning the full-length Krev-1 gene (30) into the EcoRI-XhoI sites of pGKS3 or into EcoRI-SacII sites of pGKS8, and by cloning the Ras gene into the EcoRI-XhoI sites of pEG202. Activation domain fusion plasmids have been described (29), and were obtained by cloning Krit1 (full-length) and Ra1 (Δ amino acids 1–56) genes into the EcoRI-XhoI sites of the plasmid pJG4-5 (4), and RalGDS9 (amino acids 767–848) into BamH-EcoRI sites of pYesTrp2.

Generation of Antibody Specific for cI

An essential control for generating reliable two-hybrid system Baits is the direct determination that bait-fusions are expressed and are of the correct size in yeast. This determination is best done by use of an antibody to the relevant DNA-binding domain (LexA, GAL4), as this allows comparison of a series of related Baits. To date, no antibody to cI is readily available. cI was overexpressed as a fusion protein to a 6His-tag, purified from the gel, and used as an immunogen to develop polyclonal antibodies, by contract to Research Genetics, Inc. Antibodies produced were processed and evaluated for utility in Dual Bait by standard means (44).

EXAMPLE I

Outline of Dual Bait Interaction Trap Strategy

The general approach taken with a dual bait selection strategy is outlined in FIG. 1. In the interaction trap two hybrid system (FIG. 1A, (4)), a LexA-fused bait (expressed from plasmid pEG202 or a derivative) interacts with a galactose-inducible B42 "acid blob" activation domain-fused partner (from plasmid pJG4-5) to induce the expression of two reporter genes under transcriptional control of lexA operator (op) sites, namely these are (lexAop)n-LacZ (borne on plasmid pSH18-34 (n=8), pJK103 (n=2), or pRB1840 (n=1)), and an integrated lexAop-LEU2 (in yeast strain EGY48 (n=6) or EGY191 (n=2)).

Figure 1B:
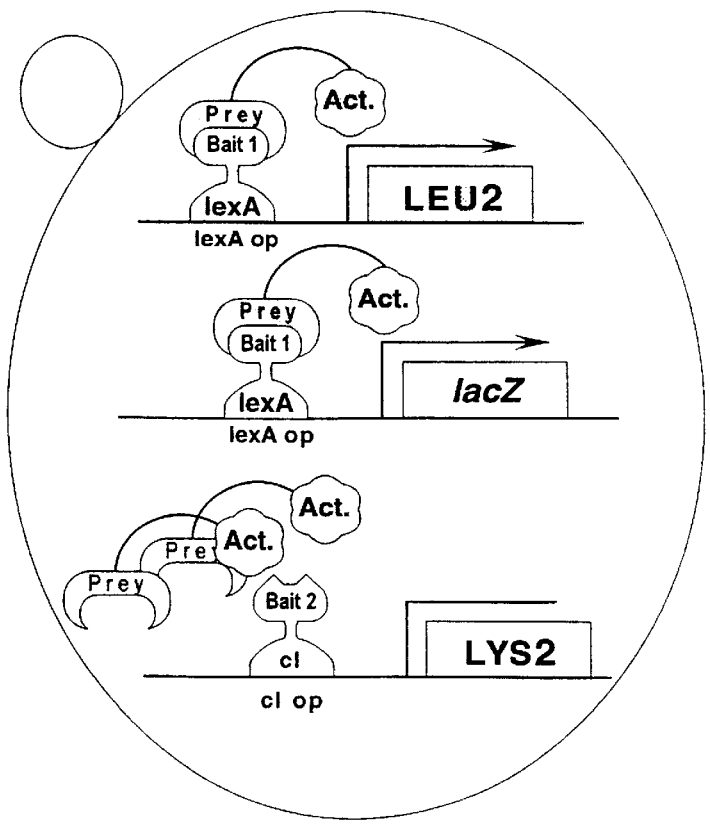
Figure 1C:
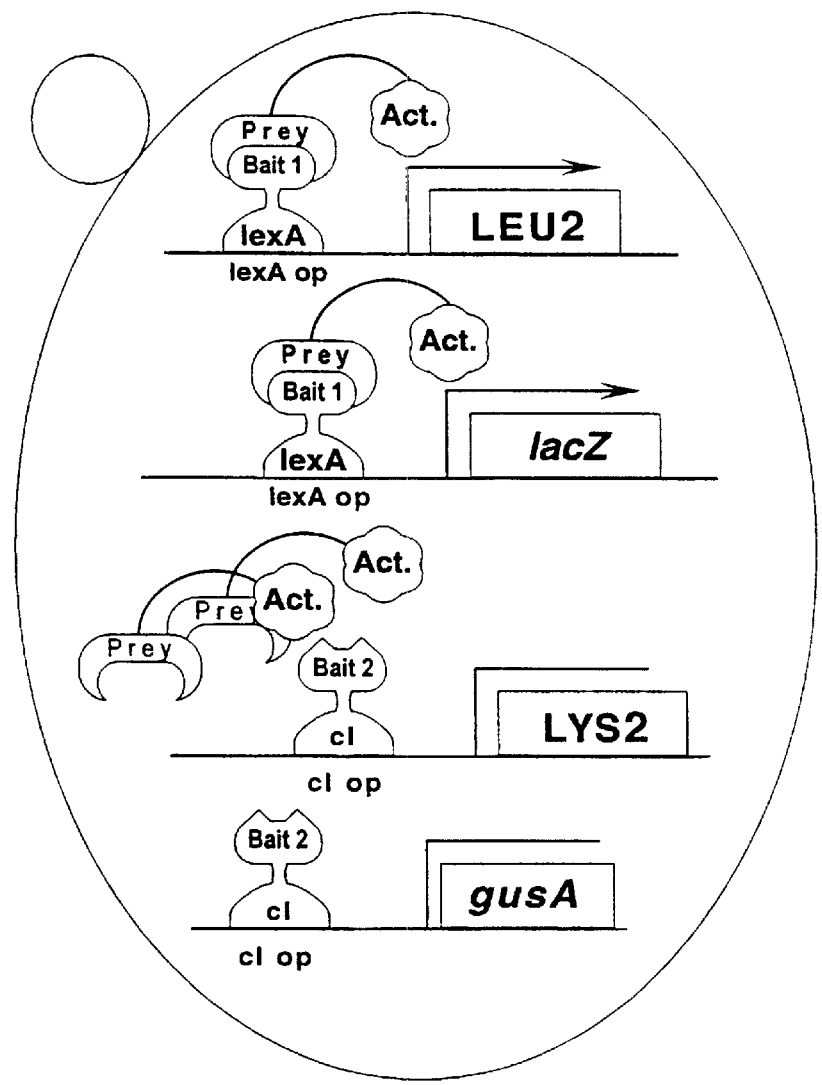
FIG. 1C shows a preferred embodiment of the invention wherein the host cell is transformed with two reporter genes fused to a first protein binding site such as the LexA operator, and two additional reporter genes fused to a second protein binding site such as the cI operator. In this embodiment, an activation domain-fused prey interacts with a LexA-fused bait to drive transcription of lexA op-responsive Leu2 and LacZ reporters, but does not interact with a cI-fused bait and thus does not turn on transcription of cI-op responsive LYS2 and GUS.

In the dual bait system here described, two further components are added (FIGS. 1B and 1C, Table 1). The first of these is a cI-fused alternate bait, expressed from the novel ZeoR, 2μ plasmid, pGKS6. The second is an additional integrated reporter system, in which 3cI operators direct the expression of the LYS2 gene, in the yeast strains SKY48 or SKY191 (derivatives of EGY48 and EGY191, respectively. These reagents can be utilized in multiple ways to enhance measurement of protein interactions over currently existing approaches.

TABLE I

Comparative activation of LacZ reporters, LexA-op versus cI-op. (Values shown reflect proportional enhancement of activation over background in β-galactosidase assays).

| | pEG202-Krit1 | | | pGKS3-Krit1 | | |
|---|---|---|---|---|---|---|
| Reporter | pRB18-40 | JK103 | pSH18-34 | cIop-lacZA | cIop-lacZA | cIop-lacZB |
| # operators | 1 | 2 | 8 | 3 (for*) | 3 (for*) | 3 (rev*) |
| Rel. act. | 10.0 | 77.7 | 132.2 | 1.0 | 94.7 | 97.6 |

*for = forward orientation
*rev = reverse orientation

As a first example, in a library screen, if an activation domain-fused interacting protein associates uniquely with a LexA-fused primary bait but not with a cI-fused alternate bait, SK48 or SKY191 yeast containing the appropriate bait and reporter constructs would turn blue on medium containing XGal, and grow on medium lacking leucine, but fail to grow on medium lacking lysine; in contrast, promiscuously interacting clones would be revealed by their growth on medium lacking both leucine and lysine. Alternatively, yeast expressing the LYS2 gene could be selected against by inclusion of the α-aminoadipate in the growth medium as the sole source of nitrogen (31). By either strategy, false positives would be eliminated simultaneously with isolation of true positive clones.

As a second example, in targeted examination of the interaction of a single activation-domain fused protein with two defined partners (for example, interaction of activation-domain-fused cyclin D with LexA-fused CDK4 and cI-fused CDK6), a randomly mutagenized pool of activation-domain-fused partners could be screened to identify mutations that disrupt interaction with either one or both of the partner proteins.

As a third example, one area of application of two-hybrid systems is in drug screening to identify compounds that disrupt interactions between discrete pairs of interacting proteins (8, 32, 33); dual bait reagents would apply a simultaneous control to the specificity of such interactions.

Parallel Performance of LexA and cI Expression and Reporter Systems

Figure 2:
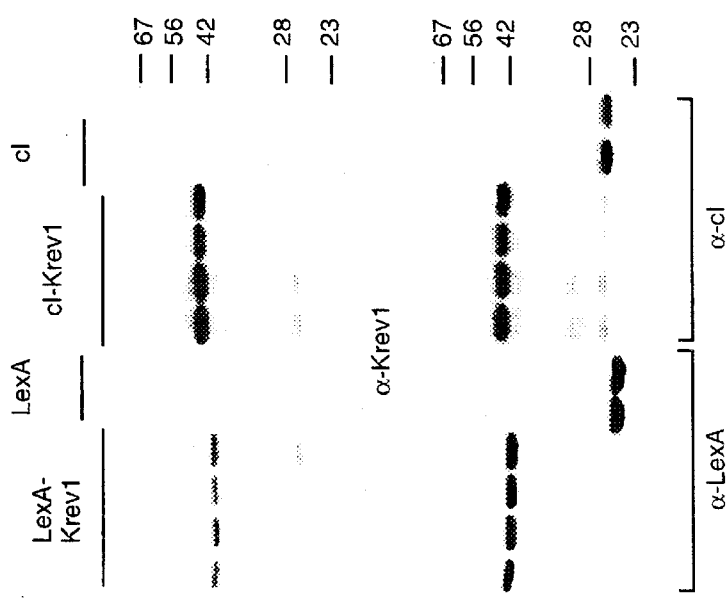
FIG. 2 is an immunoblot showing that LexA and cI expression vectors synthesize comparable levels of fusion protein. Whole cell extracts from yeast expressing either pEG202-Krev-1 (LexA-Krev-1), pGKS3-Krev-1 (cI-Krev-1), or parental vectors pEG202 or pGKS3 were examined by protein immunoblot with the antibodies to Krev-1 (top panel); the blot was then subsequently stripped, and reprobed with antibodies to LexA (bottom left) and cI (bottom right). An identically loaded gel was stained with aqueous Comassie to confirm equivalent protein loading in all lanes (not shown).

Given that assessment of protein interactions in two-hybrid systems is dependent on bait expression levels (34) and stringency of reporter systems (23), for these hypothetical uses to be practicable, the two bait-reporter combinations utilized in the dual bait system must conform relatively closely in expression levels of respective baits, and possess similar sensitivities to transcriptional activation. Accordingly, as an initial step, these parameters were carefully measured. To this end, equivalent pEG202 (LexA) and pGKS3 (cI) fusions to the protein Krev-1/rap1A (30), a human ras-family GTPase, were constructed. These and parent vectors were transformed in parallel into EGY48 yeast, and expression of the synthesized proteins assayed by Western analysis using antibodies to Krev-1, LexA, or cI. See FIG. 2. Expression of the two Krev-1 fusion constructs was found to be comparable in 4 randomly chosen colonies, with slightly higher levels (approximately 3 fold) in the cI constructs. Further, expression of the fusion protein was in each case similar to the matching unfused DNA-binding domain, indicating that cI tolerated attachment of a fusion domain without loss of stability. Finally, essentially identical expression levels were observed using pGKS6-Krev-1, a ZeoR instead of HIS3 version of pGKS3 (not shown), indicating the selectable marker could be exchanged without gross alteration of plasmid copy number.

The degree to which activation occurred through cI operators was compared to activation through LexA operators. As a conservative first step, analogous fusions of pGKS3 and pEG202 to Krit1 (a Krev-1 interacting protein (29) that fortuitously functions as a transcriptional activator of moderate strength), were constructed and assayed for the activation of the closely related cIop- and LexAop-LacZ reporters. Using EGY48 as a host, parallel transformations were performed with pGKS3-Krit1 plus cIop-LacZA and cIop-LacZB (3 cI operators, either orientation); and with pEG202-Krit1 plus pRB1840, pJKl103, or pSH18-34 (1, 2, or 8 lexAop-LacZ) (23); and as a negative control, with pEG202-Krit1 plus cIop-LacZA. β-galactosidase assays were used to measure activation of the LacZ reporters. See Table 1, above. In these tests, the cI-Krit1 fusion protein activated the two cIop-LacZ constructs to equivalent levels, which were closely comparable to that obtained using the combination of LexA-Krit1 and pJK103. As a negative control, the LexA-Krit1 construct was also shown not to activate the cIop-LacZ reporters, as expected.

Figure 3:
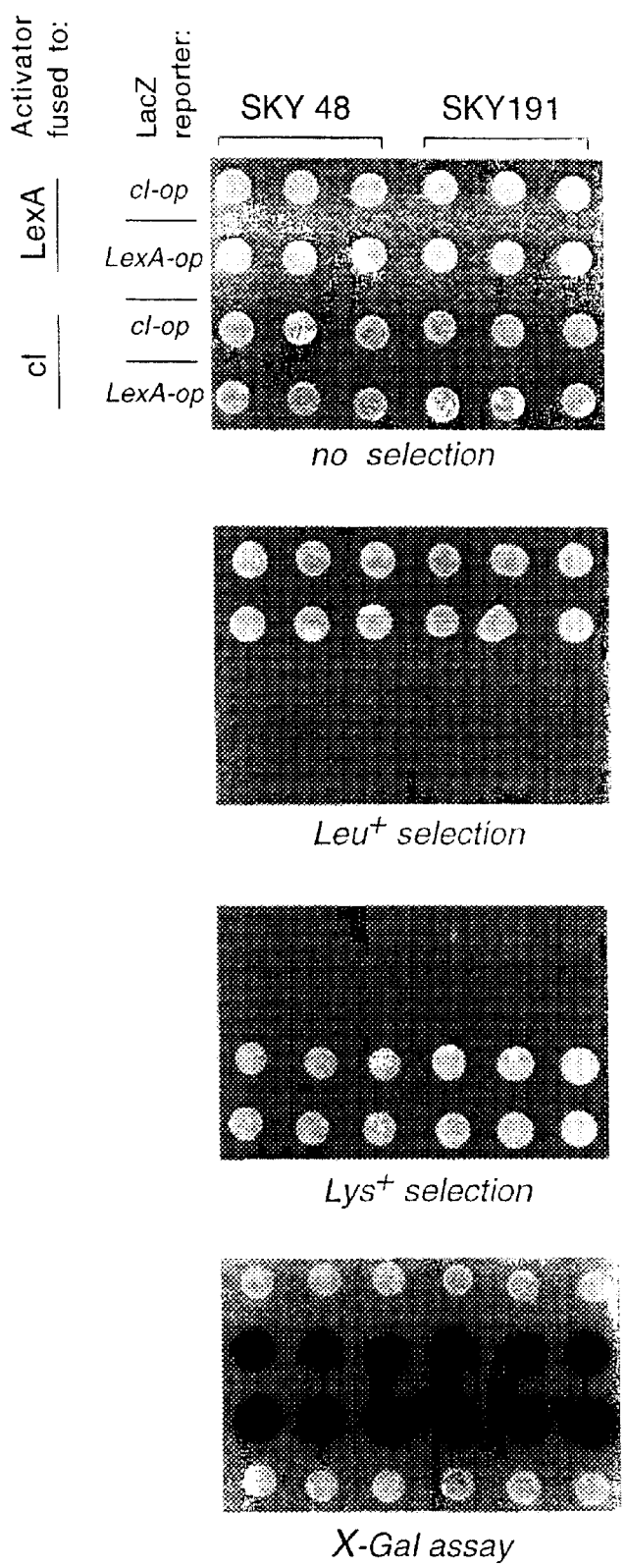
FIG. 3 is a set of photographs showing growth characteristics of yeast reporter plasmids and strains. Strains SKY48 and SKY191 were transformed with the pairwise combinations of either pEG202-Krit1 or pGKS3-Krit1, transcriptionally activating fusions to LexA and cI, respectively; and either pJK103 or pcIop-LacZA reporters with LacZ transcriptionally responsive to LexA or cI operators, respectively. Three independent transformants were replica-plated either on non-selective medium (top), or medium selecting for activation of LEU2 (leucine- , second panel), LYS2 (lysine-, third panel), and LacZ (with XGal, fourth panel) reporters.

The direct activation of LEU2 versus LYS2 auxotrophy reporters was then compared, again using analogous LexA- and cI-fused Krit1. Using SKY48 and SKYl191 as hosts, the data show that cI-Krit1 is capable of activating the LYS2 reporter of SKY strains, while LexA-Krit1 is not. Conversely, LexA-Krit1 activates the LEU2 reporter of these strains, while cI-Krit1 does not. See FIG. 3. Notably, positive growth on the LEU2 and LYS2 reporters could be assessed in a similar time frame, with results detectable at 24–48 hours after plating yeast on selective medium. Based on visual estimation of growth rate, the sensitivity of the cIop-LYS2 reporter in these strains appears to be intermediate between that of the LEU2 reporters in EGY48 and EGY191.

Cumulatively, these results indicated that the cI and LexA-based expression and reporter constructs yielded results in a similar sensitivity range, making them suitable for purposes of comparison.

Specificity of the Dual Bait System in Two-hybrid Assay

The major criterion for effective use of a dual bait system is that it should effectively discriminate interactions of a partner with related but distinct proteins. Ras and Krev-1 possess 56% amino acid identity, and are known to interact with an overlapping set of protein partners (35–37). In experiments described elsewhere (29), it has been determined that Raf preferentially interacts with Ras by two-hybrid system assay, while Krit1 preferentially interacts with Krev-1 (29). Neither Ras nor Krev-1 activates transcription when expressed as a DNA-binding-domain fusion.

The strain SKY191 with the plasmid pSH18-34 was used as a host for transformation by pEG202-Ras (LexA-Ras) and pGKS8-Krev1 (cI-Krev1). We then super-transformed the SK191/pEG202-Ras/pGKS8-Krev1 combination in parallel with each of the galactose-inducible expression plasmids pJG4-5-Raf or pJG4-5-Krit1 or pYesTrp2-RalGDS, and assayed for reporter activation/growth properties on selective medium. A schematic diagram of pGK58 is shown in FIG. 5C. As noted above, activation through a LexA-fusion permits growth on leucine-medium, and production of LacZ (cleaves XGal, Magenta-Gal, etc. to produce colored products); activation through a cI-fusion permits growth on lysine-medium, and production of β-glucuronidase (cleaves XGluc, etc., to produce colored products). The results are presented in FIG. 4.

Figure 4:
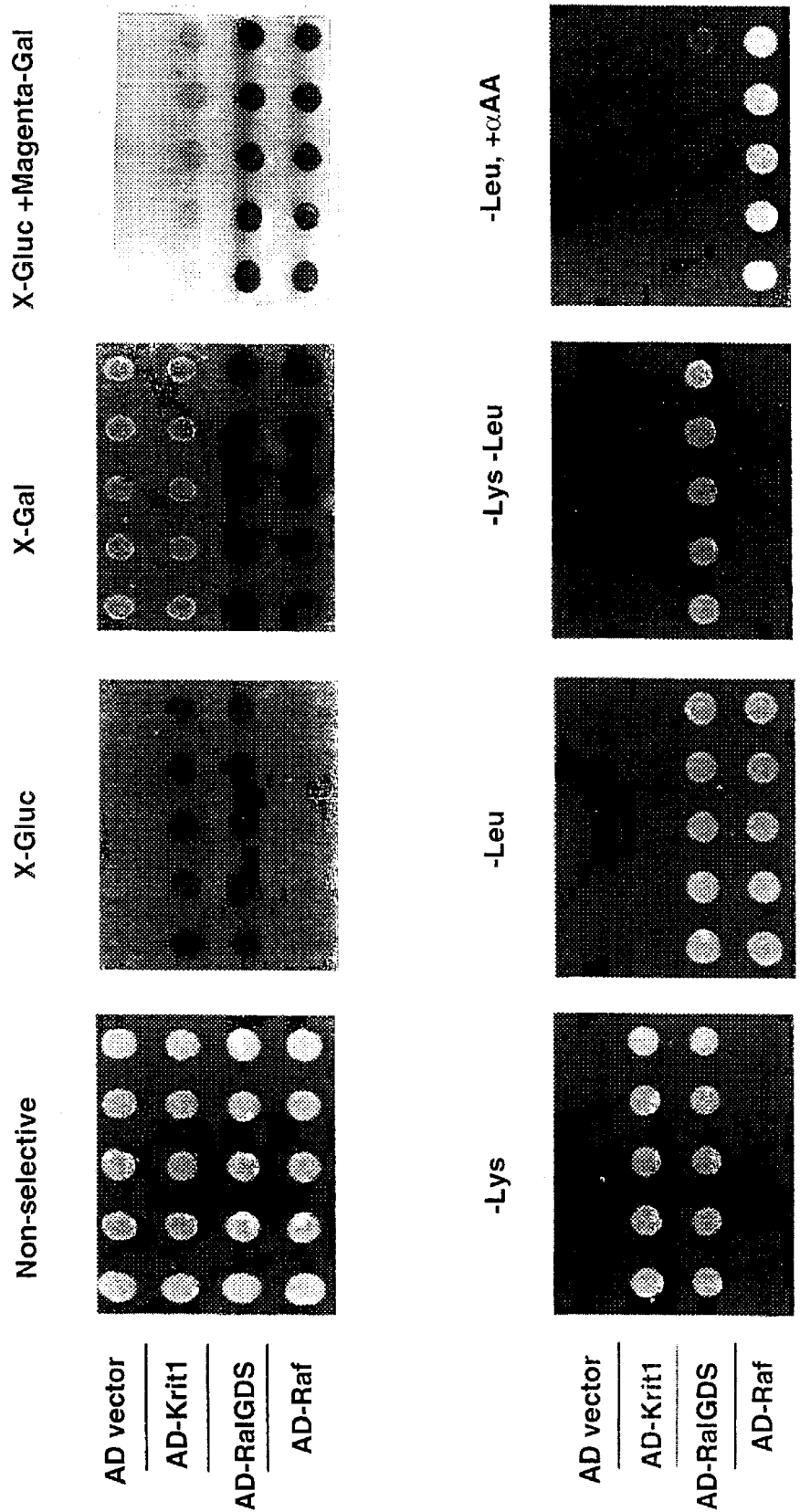
FIG. 4 is a set of photographs showing growth characteristics of yeast reporter plasmids and strains. The strain SKY191 with the plasmid pSH18-34 was used as a host for transformation by pEG202-Ras (LexA-Ras) and pGKS8-Krev1 (cI-Krev1). We then super-transformed the SK191/pEG202-Ras/pGKS8-Krev1 combination in parallel with each of the galactose-inducible expression plasmids pJG4-5-Raf or pJG4-5-Krit1 or pYesTrp2-RalGDS. Panel a, growth on non-selective media; Panel b—growth on X-Gluc; Panel c—growth on X-gal; Panel d—growth on X-Gluc+Magenta-Gal; Panel e—growth on Lysine free media; Panel f—growth on Leucine free media; Panel g—growth on Lysine-free/Leucine free media and Panel h growth on Leucine-free+α-aminoadipate as the sole source of nitrogen.

All yeast grew on non selective plates (UHW, glucose or galactose, FIG. 4, panel a). No strains grew on either leucine- or lysine- plates when glucose was present as carbohydrate source. However, under galactose-induction, strains containing pJG4-5-Raf were able to grow preferentially on leucine-medium (FIG. 4, panel f), but only minimally on lysine-medium, based on association between Raf and LexA-Ras; conversely, strains containing pJG4-5-Krit1 grew well on lysine-medium, but only weakly on leucine-medium, based on interaction between Krit1 and cI-Krev-1 (FIG. 4, panel e). Strains containing pYesTrp2-RalGDS grew well on both lysine- and leucine-medium (FIG. 4, panels e, f), while a negative control (strains containing empty plasmid pJG4-5) did not grow on any selective plates (FIG. 4, panels e, f). Interaction of RalGDS with both baits could be also detected on the double-auxotrophic lysine-leucine-plate, where this was the sole plasmid combination resulting in growth (FIG. 4, panel g). Interactors that associated with only the cI-fused bait, or non-selectively with both the cI- and LexA-fused baits could be counterselected by inclusion of the α-aminoadipate in the growth medium as the sole source of nitrogen (FIG. 4, panel h).

Results of Xgal and Xgluc assay on the plates are in good correspondence with the auxotrophic selection assay, with Raf-Ras positive with XGal (FIG. 4, panel c), Krev-1Krit1 positive with XGluc (FIG. 4, panel b), and Ral-GDS positive with both (FIG. 4, panel b,c). Note, using a complementary set of color producing substrates, (Magenta-Gal+XGluc) both LacZ and GusA activities can also be assayed on a single plate (FIG. 4, panel d). These results confirmed that a dual bait system can be used to distinguish interactions between two closely related potential partner proteins.

EXAMPLE II

Genomic Analysis Using Dual Bait Interaction Trap Reagents

A major advantage of the Dual Bait System is its ability to minimize by half the work involved in the identification and characterization of protein-protein interactions. The improved system may be applied in genomic applications by allowing two simultaneous library screens to be undertaken with a single library transformation (selecting in one case for LEU+LacZ, and in the second case for LYS2+GUS), each controlled against the other for the isolation of false positives or other proteins that interact with multiple proteins.

We know from previous efforts that Krit1, which possesses multiple amino-terminal ankyrin repeats, while yielding some biologically appropriate interactors, also yields a high frequency of false positives when used as a two-hybrid system bait (data not shown). Most of these can be readily excluded because they also interact with the non-specific bait protein LexA-bicoid. As a second, more stringent type of test, the SKY+LexA/cI-op vector yeast containing LexA-Krit1 and cI-bicoid will be utilized to screen a HeLa library in a search for cDNAs that have a LEU2+LacZ+, LYS2-GUS-phenotype. The results obtained will be compared with prior results from conventional Interaction Trap, to determine whether the majority of false positives have been eliminated while retaining apparently specific interactors. Further, LYS2 expression can be counterselected by inclusion of the toxic metabolite α-aminoadipic acid in growth medium. We will determine whether selection of positives on leucine-, XGal+plates containing α-aminoadipic acid is sufficient to eliminate false positive cDNAs that interact with both Krit1 and bicoid.

Finally, to assess the specificity of these interactions these key experiments would be repeated with a second set of matched proteins with overlapping interaction specificities. These would include either the Myc-Max-Mxil set of helix-loop-helix proteins previously used to calibrate the Interaction Trap (6), or part of the set of Cdk-Cdi interactors described as a control set for interaction mating (8).

As a further demonstration of the enhanced specificity achievable using the improved reagents of the present invention, the capacity of the Dual Bait system was tested by performing a dual library screen with yeast containing LexA-Dimit and cI-hsDim1 as baits. Dimit is a novel splicing factor-like protein (Zhang and Golemis, unpublished), isolated as an interactor of hsDim1. hsDim1 is a human member of a highly conserved family of proteins implicated in regulation of cell cycle progression, although currently of unknown means of function (41).

SKY191 cells were transformed with pMW103-Dimit (LexA-Dimit), pGKS8-1-Dim1 (cI-Dim1), and pMW109 (a lexAop-LacZ reporter). We used this strain to screen a HeLa cDNA library to identify novel partner proteins. Positives were selected on Leu- and Lys-plates and then retested by replica technique for the activation of each of the four reporters. Screening for potential Dim1 partners on lysine-plates did not result in the isolation of any true interactors from this library (i.e., no galactose-specific positives were obtained). However, a large number of potential partners were identified for Dimit: prior to analysis of the library-encoded cDNAs, we were able to use phenotype of the second set of reporters to identify a set of 23 clones that were specific for Dimit versus Dimit+Dim.

Of the 23, the 6 which interacted with the highest affinity as assayed by two-hybrid were proved to be multiple independent isolates encoding a full length cDNA for Dim1, the protein originally used to isolate Dimit, and hence likely to be a true interacting partner for the protein. Further, in structural studies of Dim1 in progress (Zhang and Golemis, unpublished), we have found that in vitro expressed Dim1 does not homodimerize even when expressed at millimolar levels: validating the specificity of these pJG4-5-Dim1 clones for LexA-Dimit, but not for cI-Dim1, as observed in the screen. Of the other clones emerging from the screen, at least one gene (Peroxisome associated gene) is a good candidate for biological interactions with Dimit, based on characterization to date; others represent multiple isolates of as yet uncharacterized genes; and only one is an obvious false positive (ferritin, frequently isolated in this assay (4)). Thus, using Dual Bait system allowed us to reduce the number of false positives isolated in a two-hybrid screen.

EXAMPLE III

Isolation and Characterization of RNA Binding Proteins Using Dual Bait Interaction Trap Methods have been described which utilize two-hybrid related technologies to study RNA-protein interactions. In a standard application, the bait protein (now termed "hook") is a DNA-binding domain fused to a known RNA binding protein (the stem loop of MS2 is generally used). A separate promoter is used to highly express an RNA containing a binding site for MS2, (e.g., MSE), fused to the RNA consensus sequence for which a protein partner is desired. In this example, such an RNA is referred to as a "bait". A standard activation domain fused library forms the third component, as with the two hybrid system. In cases where an RNA-binding protein of the appropriate specificity is encoded by the library, it interacts with the consensus sequence, while the MS2 DNA element interacts with the MS2-DNA-binding domain fusion, bringing the activator to DNA and turning on the reporters. While this approach has been successfully used to screen libraries in some cases (42), it is known to be prone to a large number of false positives, representing proteins with a non specific RNA-binding capacity. The dual bait system of the prsesent invention may be used to advantage to reduce this background of false positives.

In a standard approach, a LexA-MS2 fusion would constitute hook 1, while a cI-tat fusion protein would constitute hook 2 (tat-tar interactions have been demonstrated previously). Bait 1 would be a MSE-specific consensus RNA sequence; bait 2 could be a tar-non-specific RNA consensus sequence. As for a protein based Dual Bait, specific interactors would be defined as those which interact with the specific RNA sequence to activate LEU2 and LacZ, but not with the non-specific RNA to activate LYS2 and GUS.

EXAMPLE IV

Identificaion and Charaterization of Mutations Specfically Disrupting Interactions with One Partner A key genomic application for two-hybrid systems will be their use in assigning small sequence differences that contribute to differential interaction affinities between protein family members; or identifying mutations that disrupt interactions between a test protein and one of two distinct interacting partner proteins. A related application might be the use of two-hybrid systems to screen for pharmaceutical agents that disrupt or enhance the interaction of a test protein with partner A, but not related partner B. For all of these applications, it is particularly desirable to be able to do the experiment with all interacting components present in a single yeast cell, as this will eliminate variance due to mutations in the yeast affecting such parameters as drug permeability or growth rate. We will determine whether the Dual Bait system is effective for such applications.

To demonstrate the feasibility of this approach, the following experiments were performed. The p2-activated kinases (Paks 1, 2, and 3) associate with activated Cdc42 and Rac1 (43). Other proteins, with similar p21-binding domains, can associate selectively with either Cdc42 or Rac1, but not both. These facts suggest that it may be possible to mutate Pak such that it selectively binds to only one of these GTPases. Such a reagent would be valuable for many reasons, e.g, one might use pieces of the resultant mutant to selectively block Cdc42 vs Rac signals. Here, Cdc42 and Rac1 have been transfomed into yeast as cI- and LexA-fused baits, correspondingly, and a library of mutated Pak1 was screened to find interactors with increased specificity towards Cdc42 or Rac1.

SKY48 cells were transformed with pEG202:Rac1$^{L61}$, pGKS8-1:Cdc42$^{L61}$, and pSH-18-34 (the L61 mutation represents a kinase-dead form of the protein, known to generally stabilize interaction affinity, in a non-specific manner).

To create a library of mutated Pak1 in the activation-domain fusion plasmid pJG4-5, mutagenic PCR of Pak1 inserts was performed in the presence of MnCl$_2$ and unequal dNTP levels, to increase the misincorporation rate for Taq polymerase. Purified PCR products and EcoRI-XbaI digested pJG4-5 were co-transformed in the baits/reporter-bearing SKY48 cells, yielding about 10,000 colonies as the result of homologous recombination between the pJG4-5 vector and the Pak1 PCR product (which has about 150 bp overlap at the 5' and 3' ends with pJG4-5). These colonies were then tested for the loss of interactions between Cdc42 and Pak1 and/or Rac1 and Pak1 using replica technique. Cdc42/Pak1 interactions score as growth on leucine-minus media, and light blue color on X-Gal media. Rac1/Pak1 interactions score as growth on lysine-minus media, and dark blue color on X-Glu media. Twenty-one Rac1$^-$/Cdc42$^-$ and twenty-four Rac1$^-$/Cdc42$^+$ clones were recowered. Western blotting was used to confirm the expression of both baits and to assess the expression/size of the potential Pak1 mutants. The pJG4-5 inserts from the corresponding clones were isolated using PCR from yeast lysates, purified and sequenced. All sequenced clones contained mutation(s) in the coding region of Pak1; mutations introducing stops/frameshifts coincided with the clones expressing truncated forms of Pak1, as ascertained by Western; non-identical sets of mutations were obtained with specificity for Rac1 versus Cdc42. The obtained mutations are now being processed for analysis in an independent assay system (e.g., pull-downs, Co-IPs, etc) to confirm their properties.

The present invention is directed to the development and characterization of novel dual bait reagents that can be used to study the interaction of a protein with two distinct partners in a single yeast cell. Such reagents may be incorporated into a kit that may be used to advantage to augment yeast interaction trap kits currently commercially available. The cI repressor/cI operator system utilized in the SKY yeast strains and cIop-LacZ plasmids is demonstrated to function with a sensitivity range closely comparable to the pre-existing LexA repressor/operator system in the interaction trap, facilitating their combined use. In a model system assaying the interaction of the related GTPases Ras and Krev-1 with their specific partners Raf and Krit1, the dual bait system clearly differentiates high affinity versus lower affinity interactions. Table II provides a list of reagents that may be used to advantage in practicing the methods of the present invention.

TABLE II

| Name | Genotype/Phenotype |
|---|---|
| Plasmids for LYS2 integration | |
| pCIL-1 | $Ap^R$ URA3 cIop-LYS2 |
| pCIL-2 | $Ap^R$ TKL2' cIop-LYS2 |
| Reporter plasmids | |
| cIop-LacZA | $2\mu$ URA3 $Ap^R$ cIop lacZ (both |
| cIop-LacZB | orientation of CI operators) |
| cIop-gusA | ARS-CENURA3 $Ap^R$ cIop-gusA |
| pRG2,3,4,5,6 | $2\mu$ URA3 $Km^R$ cIop-gusA |
| pRG31 | $2\mu$ URA3 $Km^R$ cIop-gusA |
| Plasmids for cI-Bait fusion expression | |
| pGKS8-1a,b | $2\mu$ $Zeo^R$ cIop-gusA |
| pGKS8-3a,b | $2\mu$ $Zeo^R$ cIop-gusA |
| pGKS3,5 | $2\mu$ HIS3 $Ap^R$ |
| pGKS6a,b,c | $2\mu$ $Zeo^R$ |
| pGKS7a,b | $2\mu$ $Zeo^R$ (lower expression of cI fusion than in pGKS7) |
| Yeast strains | |
| SKO1 | MATa trp1 ura3 his3 leu2 lys2Δ201 URA3:cIop-LYS2 |
| SK10 | MATa trp1 ura3 his3 6lexAop-LEU2 lys2Δ201 URA3:cIop-LYS2 |
| SKY48 | MATα trp1 ura3 his3 6lexAop-LEU2 cIop-LYS2 |
| SKY191 | MATα trp1 ura3 his3 2lexAop-LEU2 cIop-LYS2 |
| Control set of plasmids: | |
| pGKS3:Krit | activating HIS3 $Ap^R$ |
| pGKS3:Krev | non-activating HIS3 $Ap^R$ |
| pGKS8-1:Krev | non-activating $Zeo^R$ |
| pEG202:Ras | non-activating HIS3 $Ap^R$ |
| pJG4-5:Krit | Krev interacting |
| pJG4-5:Raf | Ras interacting |
| pYesTrp:Ra1GDS | Krev & Ras interacting |

Note: a,b,c versions differ in polylinker frames only; pGKS3,5 differ in polylinker sequences only.

Figure 6:
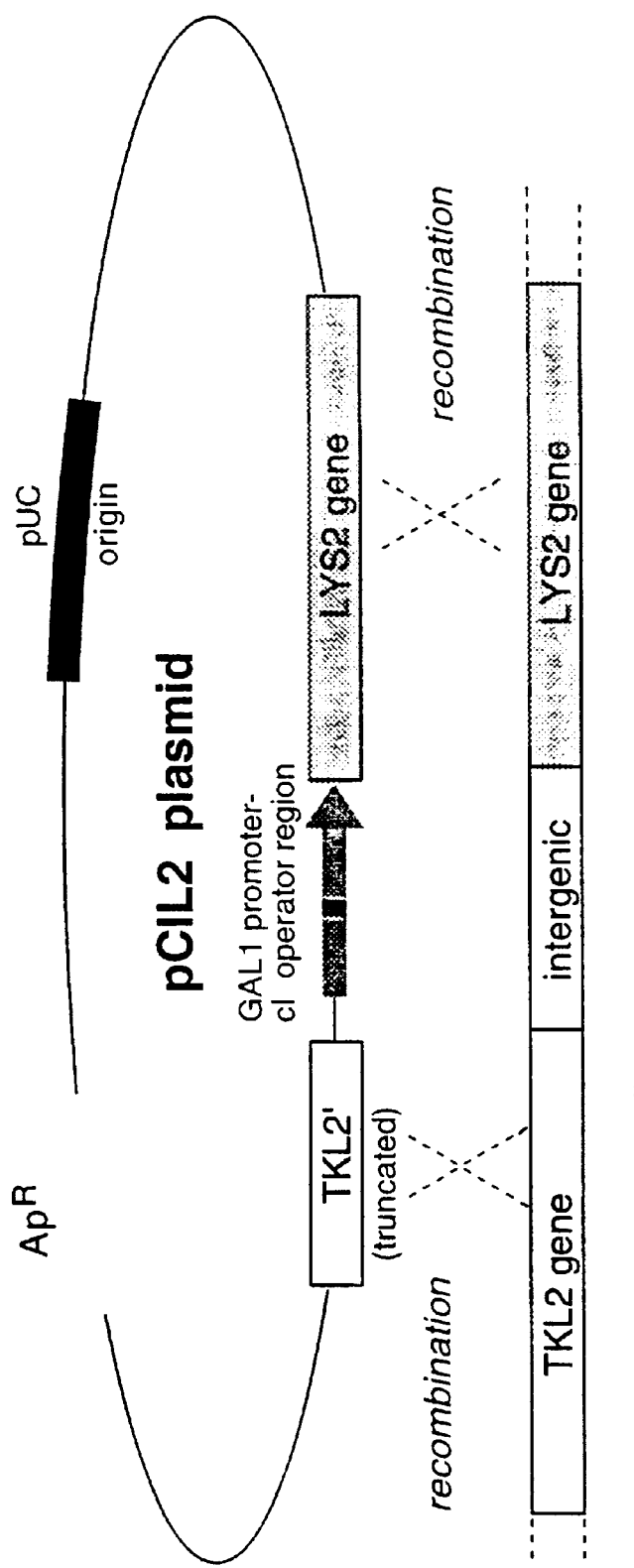
FIG. 6 shows a schematic drawing of the pCIL2 plasmid of the present invention. This plasmid enables selection on 0.2% DL(α) aminoadipic acid as the sole source of nitrogen.

PRG2,3,4,5,6 plasmids differ in orienttion of gusA cassett and/or an extra terminator;

pRG5 and pRG6 provide lower background levels of gusA activity.

pRG31 is the first of the series of reporters with varying sensitivity, which utilize the optimized cI operator sequence(s) as opposed to the natural casssette of $OR_1OR_2OR_3$ operators of λ phage. There is a mating partner for SKY strains available (constructed in the lab of Randy Strich): his 3-1 leu2-3, 112 trp1-1 ura3-1 2LexAops::LEU2 lys2-1 A schematic diagram of the pCIL-2 plasmid is shown in FIG. 6.

By introducing an internal gauge of interaction selectivity, the dual bait reagents described in the present invention both allow a single step elimination of false positives arising in two-hybrid screens, and also provide a new class of applications for two-hybrid systems over those currently achievable. As noted above, these include mutational analysis of protein-specific interaction domains, and high-throughput specific protein-drug screening efforts. Alternatively, the reporter system developed in this study on an interaction trap backbone (4) purposely uses a DNA-binding domain (cI), reporter gene (LYS2) and plasmid marker (zeocin resistance) not in use in any other two-hybrid based system (2, 3, 5), including the recently described membrane-based SOS system (38). Thus, these reagents could theoretically be added on to any of the other screening systems; in the case of the SOS-system, this raises the possibility that with minor modification of library vector, a single bait could be simultaneously used to identify interactors using either a membrane-based or a transcriptional-activation-based selection strategy, enlarging the potential pool of interacting proteins obtained. Although the dual bait reagents described herein have been optimized for use in conjunction with LexA-fusions, parameters have been previously established to test and vary sensitivity levels (23), making merging of two-hybrid systems a beneficial advance in the biochemical elucidation of the important protein-protein interactions involved in the regulation of cell growth and metabolism.

REFERENCES

1. Fields, S. & Song, O. (1989) Nature 340, 245–246.
2. Chien, C. T., Bartel, P. L., Sternglanz, R. & Fields, S. (1991) Proc. Nat. Acad. Sci. USA 88, 9578–9582.
3. Durfee, T., Becherer, K., Chen, P. L., Yeh, S. H., Yang, Y., Kilburn, A. E., Lee, W. H. & Elledge, S. J. (1993) Genes Dev 7, 555–569.
4. Gyuris, J., Golemis, E. A., Chertkov, H. & Brent, R. (1993) Cell 75, 791–803.
5. Vojtek, A. B., Hollenberg, S. M. & Cooper, J. A. (1993) Cell 74, 205–214.
6. SenGupta, D. J., Zhang, B., Kraemer, B., Pochart, P., Fields, S. & Wickens, M. (1996) Proc. Nat. Acad. Sci. USA 93, 8496–8501.
7. Wang, Z. F., Whitfield, M. L., Ingledue, T. C. 3., Dominski, A. & Marzluff, W. F. (1996) Genes Dev. 10, 3028–3040.
8. Licitra, E. J. & Liu, J. O. (1996) Proc. Nat. Acad. Sci. USA 93, 12817–12821.
9. Colas, P., Cohen, B., Jessen, T., Grishina, I., McCoy, J. & Brent, R. (1996) Nature 380, 548–550.
10. Yang, M., Wu, Z. & Fields, S. (1995) Nuc. Acids Res. 23, 1152–1156.
11. Osborne, M., Dalton, S. & Kochan, J. P. (1995) Bio/Technology 13, 1474–1478.
12. Osborne, M. A., Zenner, G., Lubinus, M., Zhang, X., Songyang, Z., Cantley, L. C., Majerus, P., Burn, P. & Kochan, J. P. (1996) J. Biol. Chem. 271, 29271–29278.
13. Finley, R. & Brent, R. (1994) Proc. Nat. Acad. Sci. USA 91, 12980–12984.
14. Bartel, P. L., Roecklein, J. A., SenGupta, D. & Fields, S. (1996) Nature Genet. 12, 72–77.
15. Fromont-Racine, M., Rain, J.-C. & Legrain, P. (1997) Nat. Gen. 16, 277–282.
16. Serebriiskii, I. & Golemis, E. A. (1996) http://www.fccc.edu/research/labs/golemis/InteractionT rapInWork.html.
17. Alt, F. W., DePinho, R., Zimmerman, K., LeGouy, E., Hatton, K., Ferrier, P., Tesfaye, A., Yancopoulos, G. & Nisen, P. (1986) CSH Symp. Quant. Biol. LI, 931–941.
18. Meyerson, M., Enders, G. H., Wu, C.-L., Su, L.-K., Gorka, C., Nelson, C., Harlow, E. & Tsai, L.-H. (1992) EMBO J 11, 2909–2917.
19. Shalloway, D. & Taylor, S. J. (1997) TICB 7, 215–217.
20. Golemis, E. A., Serebriiskii, I., Gyuris, J. & Brent, R. in Current Protocols in Molecular Biology (eds. Ausubel, F. M.) 20.1.1–20.1.35 (John Wiley and Sons, New York, 1997).

21. Ausubel, F. M., Brent, R., Kingston, R., Moore, D., Seidman, J., Smith, J. A. & Struhl, K. Current Protocols in Molecular Biology (John Wiley & Sons, New York, 1987-present).
22. Sherman, F., Fink, G. & Hicks, J. B. Methods in yeast genetics (Cold Spring Harbor Laboratory, Cold Spring Harbor, N.Y., 1986).
23. Estojak, J., Brent, R. & Golemis, E. A. (1995) Mol. Cell. Biol. 15, 5820–5829.
24. Duttweiler, H. M. (1996) TIG 12, 340–341.
25. Ptashne, M. in The Operon (eds. Miller, J. H. & Reznikoff, W. S.) 325–344 (Cold Spring Harbor Press, Cold Spring Harbor, N.Y., 1978).
26. Markham, B. E., Little, J. W. & Mount, D. W. (1981) Nucl. Acids Res. 9, 4149–4161.
27. Little, J. W., Mount, D. W. & Yanisch-Perron, C. R. (1981) Proc. Nat. Acad. Sci. USA 78, 4199–4203.
28. Brent, R. & Ptashne, M. (1981) Proc. Nat. Acad. Sci. USA 78, 4204–4208.
29. Serebriiskii, I., Estojak, J., Sonoda, G., Testa, J. R. & Golemis, E. A. (1997) Oncogene 15:1043–1049.
30. Kitayama, H., Sugimoto, Y., Matsuzaki, T., Ikawa, Y. & Noda, M. (1989) Cell 56, 77–84.
31. Chattoo, B. B., Sherman, F., Azubalis, D. A., Fjellstedt, T. A., Mehnert, D. & Ogur, M. (1979) Genetics 93, 51–65.
32. Chiu, M. I., Katz, H. & Berlin, V. (1994) Proc. Nat. Acad. Sci. USA 91, 12574–12578.
33. Mendelsohn, A. R. & Brent, R. (1994) Curr. Opin. Biotech. 5, 482–486.
34. Golemis, E. A. & Brent, R. (1992) Mol. Cell. Biol. 12, 3006–3014.
35. Frech, M., John, J., Pizon, V., Chardin, P., Tavitian, A., Clark, R., McCormick, F. & Wittinghofer, A. (1990) Science 249, 169–171.
36. Herrmann, C., Horn, G., Spaargaren, M. & Wittinghofer, A. (1996) J. Biol. Chem. 271, 6794–6800.
37. Zhang, X.-f., Settleman, J., Kyriakis, J. M., Takeuchi-Suzuki, E., Elledge, S. J., Marshall, M. S., Bruder, J. T., Rapp, U. R. & Avruch, J. (1993) Nature 364, 308–313.
38. Aronheim, A., Zandi, E., Hennemann, H., Elledge, S. J. & Karin, M. (1997) Mol. Cell. Biol. 17, 3094–3102.
39. Chalfie, M., Tu, Y., Euskirchen, G., Ward, W. W. & Prasher, D. C. (1994) Science 263, 802–805.
40. Aflalo, C. (1990) Biochemistry 29, 4758–4766.
41. Berry, L D et al., (1997) J. Cell Biol. 137:1337–1354.
42. Wang et al., (1996) Genes Dev. 10:3028–3040.
43. Sells, M. A., and Chernoff, J., (1997) Trends Cell Biol. 7:162–167.
44. Ausubel, F. M. et al. Eds. Current Protocols in Molecular Biology, John Wiley & Sons, N.Y.

While certain preferred embodiments of the present invention have been described and specifically exemplified above, it is not intended that the invention be limited to such embodiments. Various modifications may be made to the invention without departing from the scope and spirit thereof as set forth in the following claims.

What is claimed is:

1. A method for determining whether a first protein physically and specifically interacts with a second protein, comprising:
   a) providing a host cell which contains
      i) a first reporter gene operably linked to a first protein binding site;
      ii) a second reporter gene operably linked to said first protein binding site;
      iii) a third reporter gene operably linked to a second protein binding site, said first, second and third reporter genes encoding different reporter molecules, and said first and second protein binding sites being bound by different first and second proteins;
      iv) a first bait protein encoded by a first fusion gene, said first bait protein comprising said first protein covalently bonded to a first binding moiety which effects specific binding of said first bait protein to said first protein binding site;
      v) a second fusion gene which encodes a second fusion protein, said second fusion protein comprising said second protein which is suspected of interacting with said first bait protein, said second protein being covalently bonded to a gene activating moiety;
      vi) a second bait protein encoded by a third fusion gene, said second bait protein being different from said first bait protein and covalently bonded to a second binding moiety which effects specific binding of said second bait protein to said second protein binding site; and
   b) measuring interaction of said first and second proteins via selective activation of said first, second and third reporter genes, specific interaction between said first and second proteins being indicated by activation of said first and second reporter genes to the exclusion of activation of said third reporter gene.

2. A method as claimed in claim 1, further comprising a fourth reporter gene operably linked to said second protein binding site, said fourth reporter gene encoding a reporter which differs from the reporters encoded by said first, second and third reporter genes.

3. A plasmid for use in the method of claim 1, said plasmid being selected from the group of plasmids consisting of pGKS8-1, pGKS6, pGKS3, and pCIL-2.

4. A yeast strain for use in the method of claim 1 selected from the group of yeast strains consisting of SKY48 and SKY191.

5. A kit for practicing the method of claim 1, said kit comprising a container, plasmid pGKS8-1, a protocol for practicing the method and yeast strain SKY48.

6. The method as claimed in claim 1, wherein said first reporter is leu2, said second reporter is lacZ and said third reporter is lys2.

7. A method as claimed in claim 1, wherein said host cell is a yeast cell.

8. A method as claimed in claim 1, wherein said first protein binding site is a lexA site and said first protein binding moiety is a lexA binding protein.

9. A method as claimed in claim 1, wherein said second protein binding site is a cI op site and said second protein binding moiety is a cI binding protein.

10. The method as claimed in claim 2, wherein said fourth reporter is gusA.

11. A method for determining whether a first bait protein physically and specifically interacts with a second prey protein, comprising:
   a) providing a yeast cell which contains
      i) a first leu2 reporter gene operably linked to a lexA protein binding site;
      ii) a second lacZ reporter gene operably linked to said lexA protein binding site;
      iii) a third lys2 reporter gene operably linked to a cI op site;

iv) a first bait protein encoded by a first fusion gene, said first fusion gene encoding said first bait protein operably linked to a lexA protein binding moiety, said lexA binding moiety effecting specific binding of said first bait protein to said lexA protein binding site present on said first and second reporters;

v) a second fusion gene which encodes a second fusion protein, said second fusion protein comprising the prey protein suspected of interacting with said first bait protein, said prey protein being operably linked to a GAL4 activation region II gene activating moiety;

vi) a second bait protein encoded by a third fusion gene, said second bait protein being different from said first bait protein, and being operably linked to a cl protein binding moiety, said cl binding moiety effecting specific binding of said second bait protein to said cl op binding site present on said third reporter gene; and b) measuring the interaction between said first bait and second prey proteins via selective activation of said first, second and third reporter genes, specific interaction between said first bait protein and said second prey protein being indicated by activation of said leu2 and lacZ reporters to the exclusion of activation of said lys2 reporter.

12. A method as claimed in claim 11, further comprising a fourth reporter molecule, said fourth reporter molecule being gusA, said gusA being operably linked to a cl op binding site.

13. A method for determining whether members of a related family of proteins including at least two members physically and specifically interacts with a prey protein, comprising:

a) providing a host cell which contains
i) a first reporter gene operably linked to a first protein binding site specific for a first protein family member;
ii) a second reporter gene operably linked to said first protein binding site specific for a first protein family member;
iii) a third reporter gene operably linked to a second protein binding site specific for a second protein family member,
iv) a fourth reporter gene operably linked to said second protein binding site specific for a second protein family member, said reporter genes each encoding a different reporter, and said first and second protein binding sites being bound by different first and second member proteins;
v) a first bait protein encoded by a first fusion gene, said one first bait protein comprising said first related protein member covalently bonded to a first binding moiety which effects specific binding of said first bait protein to said first protein member binding site;
vi) a second bait protein encoded by a second fusion gene, said second bait protein comprising said second protein member covalently bonded to a second binding moiety which effects specific binding of said second bait protein to said second protein member binding site;
vii) a third fusion gene which encodes a third fusion protein, said third fusion protein comprising said prey protein which is suspected of interacting with at least one related member of a protein family, said prey protein being covalently bonded to a gene activating moiety; and b) measuring interaction of said first and second member proteins via selective activation of said first, second, third, and fourth reporter genes, specific interaction between said first family member protein and said prey being indicated by selective activation of said first and second reporter genes and specific interaction between said second family member protein and said prey being indicated by selective activation of said third and fourth reporter genes.

14. A method as claimed in claim 13, wherein said first and second member proteins are a wild type and mutated form of the same protein.

15. A method as claimed in claim 13, for screening pharmacological agents which modulate the interaction between said first family member and said prey and said second family member and said prey, further comprising the step of performing the method in the presence and absence of said pharmacological agent and determining whether said pharmacological agent i) modulates interaction between said first related family member and said prey as a function of activation of said first and second reporter genes and ii) modulates interaction between said second related family member and said prey as a function of activation of said third and fourth reporter genes.

16. A method for determining whether two unrelated proteins suspected of interacting with a single prey protein physically and specifically interacts said prey protein, comprising:

a) providing a host cell which contains
i) a first reporter gene operably linked to a first protein binding site specific for a first unrelated protein;
ii) a second reporter gene operably linked to said first protein binding site specific for a first unrelated protein;
iii) a third reporter gene operably linked to a second protein binding site specific for said second unrelated protein,
iv) a fourth reporter gene operably linked to said second protein binding site specific for a second unrelated protein, said reporter genes each encoding a different reporter, and said first and second protein binding sites being bound by different first and second unrelated proteins;
v) a first bait protein encoded by a first fusion gene, said one first bait protein comprising said first unrelated protein covalently bonded to a first binding moiety which effects specific binding of said first bait protein to said first unrelated protein binding site;
vi) a second bait protein encoded by a second fusion gene, said second bait protein comprising said second unrelated protein covalently bonded to a second binding moiety which effects specific binding of said second bait protein to said second unrelated protein binding site;
vii) a third fusion gene which encodes a third fusion protein, said third fusion protein comprising said prey protein which is suspected of interacting with at least one unrelated protein, said prey protein being covalently bonded to a gene activating moiety; and b) measuring interaction of said first and second unrelated proteins via selective activation of said first, second, third, and fourth reporter genes, specific interaction between said first unrelated protein and said prey being indicated by selective activation of said first and second reporter genes and specific interaction between said second unrelated protein and said prey being indicated by selective activation of said third and fourth reporter genes.

17. A method as claimed in claim 16, for screening pharmacological agents which modulate the interaction between unrelated proteins suspected of interacting with a single prey protein, further comprising the step of performing the method in the presence and absence of said pharmacological agent and determining whether said pharmacological agent i) modulates interaction between said first unrelated protein and said prey as a function of activation of said first and second reporter genes and ii) modulates interaction between said second unrelated protein and said prey as a function of activation of said third and fourth reporter genes.

18. A method for determining whether a protein encoded by a library encoding prey proteins specifically and physically interacts with at least one bait protein comprising
   a) providing a host cell which contains
      i) a first reporter gene operably linked to a first protein binding site specific for a first bait protein;
      ii) a second reporter gene operably linked to said first protein binding site specific for a first bait protein;
      iii) a third reporter gene operably linked to a second protein binding site specific for said second bait protein,
      iv) a fourth reporter gene operably linked to said second protein binding site specific for a second bait protein, said reporter genes each encoding a different reporter, and said first and second protein binding sites being bound by different first and second bait proteins;
      v) a first bait protein encoded by a first fusion gene, said one first bait protein comprising said first protein covalently bonded to a first binding moiety which effects specific binding of said first bait protein to said first protein binding site;
      vi) a second bait protein encoded by a second fusion gene, said second bait protein comprising said second protein covalently bonded to a second binding moiety which effects specific binding of said second bait protein to said second protein binding site;
      vii) a third fusion gene which encodes a third fusion protein, said third fusion protein comprising said prey protein which is suspected of interacting with at least one protein, said prey protein being covalently bonded to a gene activating moiety; and
   b) measuring interaction of said first and second bait proteins via selective activation of said first, second, third, and fourth reporter genes, specific interaction between said first bait protein and said prey being indicated by selective activation of said first and second reporter genes and specific interaction between said second bait protein and said prey being indicated by selective activation of said third and fourth reporter genes.

19. A method as claimed in claim 15, wherein said protein family members are a wild type and mutant form of the same protein.

20. A method for determining whether at least one first bait protein physically and specifically interacts with a second prey protein, comprising:
   a) providing a host cell which contains
      i) a first reporter gene operably linked to a first bait protein binding site;
      ii) a second reporter gene operably linked to said first bait protein binding site;
      iii) a third reporter gene operably linked to a second bait protein binding site, said first, second and third reporter genes encoding different reporter molecules, and said first and second bait protein binding sites being bound by different first and second bait proteins;
      iv) a first bait protein encoded by a first fusion gene, said first bait protein comprising said first protein covalently bonded to a first DNA binding moiety which effects specific binding of said first bait protein to said first protein binding site;
      v) a second fusion gene which encodes a second fusion protein, said second fusion protein comprising said second prey protein which is suspected of interacting with said at least one first bait protein, said second protein being covalently bonded to a gene activating moiety;
      vi) a second bait protein encoded by a third fusion gene, said second bait protein being different from said first bait protein and covalently bonded to a second DNA binding moiety which effects specific binding of said second bait protein to said second protein binding site; and
   b) measuring interaction of said first and second proteins via selective activation of said first, second and third reporter genes, specific interaction between said bait proteins and prey protein being indicated by activation of said first and second reporter genes to the exclusion of activation of said third reporter gene.

21. A method as claimed in claim 20 for screening pharmacological agents which modulate the interaction between said bait and prey proteins, further comprising the step of performing the method in the presence and absence of said pharmacological agent and determining whether said pharmacological agent modulates interaction between said first and second proteins as a function of expression of the first, second and third reporter genes.

* * * * *

SEQUENCE LISTING

<160> NUMBER OF SEQ ID NOS: 5

<210> SEQ ID NO 1
<211> LENGTH: 5
<212> TYPE: PRT
<213> ORGANISM: Bacteriophage Lambda

<400> SEQUENCE: 1

Leu Ala Met Cys Gly
1               5

<210> SEQ ID NO 2
<211> LENGTH: 65
<212> TYPE: DNA
<213> ORGANISM: Artificial Sequence
<220> FEATURE:
<223> OTHER INFORMATION: ATT Frame

<400> SEQUENCE: 2
gaattcaagc ttgagctcag atctcagctg ggcccggtac cgcggccgct cgagtcgacc      60
tgcag                                                                  65

<210> SEQ ID NO 3
<211> LENGTH: 21
<212> TYPE: PRT
<213> ORGANISM: Artficial Sequence
<220> FEATURE:
<223> OTHER INFORMATION: AAT Frame

<400> SEQUENCE: 3

Asn Ser Ser Leu Ser Ser Asp Leu Ser Trp Ala Arg Tyr Arg Gly Arg
1               5                   10                  15

```
Ser Ser Arg Pro Ala
        20

<210> SEQ ID NO 4
<211> LENGTH: 65
<212> TYPE: DNA
<213> ORGANISM: Artificial Sequence
<220> FEATURE:
<223> OTHER INFORMATION: GAA Frame

<400> SEQUENCE: 4
aatttggaat tcgacctcag atctcagctg ggcccggtac cgcggccgct cgagtcgacc      60
tgcag                                                                 65

<210> SEQ ID NO 5
<211> LENGTH: 21
<212> TYPE: PRT
<213> ORGANISM: Artificial Sequence
<220> FEATURE:
<223> OTHER INFORMATION: GAA Frame

<400> SEQUENCE: 5

Asn Leu Glu Phe Glu Leu Arg Ser Gln Leu Gly Pro Val Pro Arg Pro
 1               5                  10                  15

Leu Glu Ser Thr Cys
        20
```